United States Patent [19]

Steen

[11] 4,426,154

[45] Jan. 17, 1984

[54] LIQUID FLOW PHOTOMETER

[75] Inventor: Harald B. Steen, Oslo, Norway

[73] Assignee: Ernst Leitz Wetzlar GmbH, Wetzlar, Fed. Rep. of Germany

[21] Appl. No.: 285,096

[22] PCT Filed: Nov. 10, 1980

[86] PCT No.: PCT/EP80/00127

§ 371 Date: Jul. 22, 1981

§ 102(e) Date: Jul. 22, 1981

[87] PCT Pub. No.: WO81/01472

PCT Pub. Date: May 28, 1981

[30] Foreign Application Priority Data

Nov. 23, 1979 [NO] Norway ............................... 793800

[51] Int. Cl.³ .................... G01J 3/50; G01N 21/49; G01N 21/64
[52] U.S. Cl. .................................... 356/73; 356/317; 356/341; 250/461.1
[58] Field of Search .............. 356/317, 318, 338, 244, 356/73, 337, 341; 250/458.1, 459.1, 461.1, 461.2, 435, 373

[56] References Cited

U.S. PATENT DOCUMENTS

| 3,497,690 | 2/1970 | Wheeless, Jr. et al. | 356/39 |
| 3,710,933 | 1/1973 | Fulwyler | 356/73 |
| 3,770,349 | 11/1973 | Legorret-Sanchez | 356/73 |
| 3,824,402 | 7/1974 | Mullaney et al. | 356/73 |
| 3,850,525 | 11/1974 | Kaye | 356/73 |
| 3,859,526 | 1/1975 | Hirschfeld | 250/373 |
| 3,879,129 | 4/1975 | Inoue | 356/335 |
| 4,087,685 | 5/1978 | Froot | 250/461.1 |
| 4,172,227 | 10/1979 | Tyer et al. | 250/461.2 |
| 4,348,107 | 9/1982 | Leif | 356/73 |

Primary Examiner—Vincent P. McGraw
Assistant Examiner—L. A. Dietert
Attorney, Agent, or Firm—Schwartz, Jeffery, Schwaab, Mack, Blumenthal & Koch

[57] ABSTRACT

A liquid flow photometer for fluorescence light and/or scattered light measurement, having a measuring area (37) where particles (38) flow through. The device comprises a first objective (3) focussing excitation light (5) in the measuring area (37) and also collecting fluorescence light emanating from the measuring area (37). The first objective (3) is modified by a slightly transparent central stop (39) placed in the rear focal plane of the objective. The device further comprises a second objective (23) collecting the light falling within the conic sector (40) obscured by the central stop (39). This light contains partly scattered light and excitation light. The corresponding photo-electric signal is divided in a pulsed (AC) component and a constant or slowly varying (DC) component. The DC component serves to correct one or both of the AC components representing the fluorescence and scattered light intensity in order to make them independent of variations in the excitation light intensity.

6 Claims, 2 Drawing Figures

LIQUID FLOW PHOTOMETER

BACKGROUND OF THE INVENTION

The present invention relates to liquid flow photometers for fluorescence light and/or scattered light measurement, having a measuring area where particles flow through.

Liquid flow photometry is a measuring technique increasingly more often applied within several fields of cell biology, medicine and physical-chemical measurements of particles of almost any material. In a liquid flow photometer photometric signals from single particles of microscopic size are measured when they—carried by a laminar liquid flow—pass one by one through a focus of excitation light of high intensity. The particles are centered in the liquid flow by so called hydrodynamic focussing. The types of photometric signals one is able to register, are: (1) the particles' fluorescence, (2) the light scattering caused by the particles, and (3) light absorption caused by the particles. The two first of these signal types have proved to be particularly informative.

As a typical example of the application of liquid flow photometry one can mention the measuring of the content of various components, as for instance DNA or protein, in single cells. For this purpose the cells are stained with a fluorescent dye binding specifically and quantitatively to the component in question. In this way every cell passing through the photometer's excitation focus will cause a pulse of fluorescence light. This light is picked up by a light detector. The signal from this—which is proportional to the cell's content of dye and thus of the cell component in question—is measured and stored in an electronic memory according to its size—a so called multichannel pulse height analyser. In this way several thousand cells can be measured per second with very great accuracy, and a histogram of the number of cells as a function of the cell's content of the cell component in question is obtained. The excitation light scattered by the cell as it passes the photometer's focus can be registered by another detector. Depending on the scattering angle this signal gives information on the cell's cross section or volume, and also on its inner structure and density.

In most types of liquid flow photometers the excitation light is induced by a laser. The liquid flow carrying the particles passes through the laser beam. The particles' fluorescence and light scattering are registered by two separate optical systems located beside the laser beam. In certain types of such liquid flow photometers the liquid flow is a free jet in the air. In others the liquid flow passes through a closed chamber.

The types of liquid flow photometers mentioned above are complicatedly built, and this makes them very expensive and difficult to operate. A new type of liquid flow system, which can be applied as an accessory to a standard fluorescence microscope has been described in the Norwegian Patent Application No. 791229 Fitted with a suitable light detector the microscope is converted to a liquid flow photometer which,—as regards fluorescence detection—has proved to be up to the level of the far more expensive laser-based instruments, while it is also very easy to operate. As described in the above mentioned patent application, in this liquid flow system a hydrodynamically focussed flow of particles in a laminar liquid jet is induced by a nozzle. The nozzle is placed so that the liquid flow falls at an oblique angle onto a cover glass and is thus converted to a flat, laminar flow moving along the surface of the cover glass. Because they are centered in the liquid jet, the particles will flow across the glass one by one within a narrow sector. The cover glass is placed so in relation to the microscope's objective, that the particle flow on the glass passes through the objective's focus, i.e. the microscope's measuring area.

The above-described microscope has Epi-illumination, which means that the excitation light is focussed onto the measuring area by the same objective as that collecting the fluorescence light. The objective is preferably of the oil immersion type to obtain maximum numerical aperture and correspondingly high sensitivity.

The liquid flow photometer described in the above-mentioned patent application can only measure the particles' fluorescence. Another of the instrument's limitations is that the source of the excitation light is a conventional high pressure Hg- or Xe-lamp. The light intensity from such lamps may vary somewhat, partly because the lamp's arc is not completely stable, and partly because the light emission from the lamp generally decreases with the lamp's utility time. These variations reduce reproducibility of the measurements.

SUMMARY OF THE INVENTION

It is therefore an object of the present invention to provide an improved microscope-based liquid flow photometer which makes it possible to measure in combination with the particles' fluorescence light intensity also the scattered light intensity in order to obtain information on the particles' size and structure.

It is a further object of the present invention to provide a liquid flow photometer which makes it possible to measure the intensity of the excitation light in the photometer's measuring area and to apply this signal to correct the other photometric signals, i.e. fluorescence light and scattered light for variations in this intensity in order to make the instrument independent of variations in the intensity of the excitation light.

In accomplishing the foregoing objects, there has been provided in accordance with the present invention a liquid flow photometer for fluorescence light and/or scattered light measurement having a measuring area where particles flow through. The photometer comprises:

(a) a first objective focussing excitation light in the measuring area and also collecting fluorescence light emanating from the measuring area, the objective being modified by a slightly transparent central stop placed in the rear focal plane of the objective, (b) a second objective collecting the light falling within the conic sector obscured by the central stop, (c) a filter in the light path of the second objective absorbing the fluorescence light emanating from the measuring area, (d) an adjustable aperture located in the image plane of the second objective limiting the image field of the second objective to the actual width of the measuring area, (e) light detectors measuring the light intensity within the image plane of the first and second objective, and (f) electronic amplifiers following the light detectors.

According to one preferred embodiment of the invention the second objective is placed so that its object plane falls in the measuring area and that its aperture falls within the sector of the illumination field caused by the central stop.

In accordance with another embodiment of the invention the measurement of scattered light intensity produced by the particles and excitation light intensity in the measuring area is carried out by only one optical system comprising the second objective, the filters, the adjustable aperture, one of the light detectors and one of the electronic amplifiers.

According to another preferred embodiment of the invention the electronic amplifier following the light detector in connection with the second objective has separate outlets for the pulsed (AC) part and the constant or slowly varying (DC) part of the signal from the light detector, the AC-signal corresponding to the scattered light intensity and the DC-signal corresponding the excitation light intensity.

According to another aspect of the invention, there has been provided a liquid flow photometer, comprising at least one pulse height compensator correcting the AC-signals, corresponding to the fluorescence light intensity and/or to the scattered light intensity by the DC-signal corresponding to the excitation light intensity in such a way that the electronic amplification is inversely proportional to the DC-signal.

Further objects, features and advantages of the present invention will become apparent to a person skilled in the art from the detailed description of a preferred embodiment which follows, when considered together with the attached figures of drawings.

DETAILED DESCRIPTION OF THE PREFERRED EMBODIMENT

Figure 1:
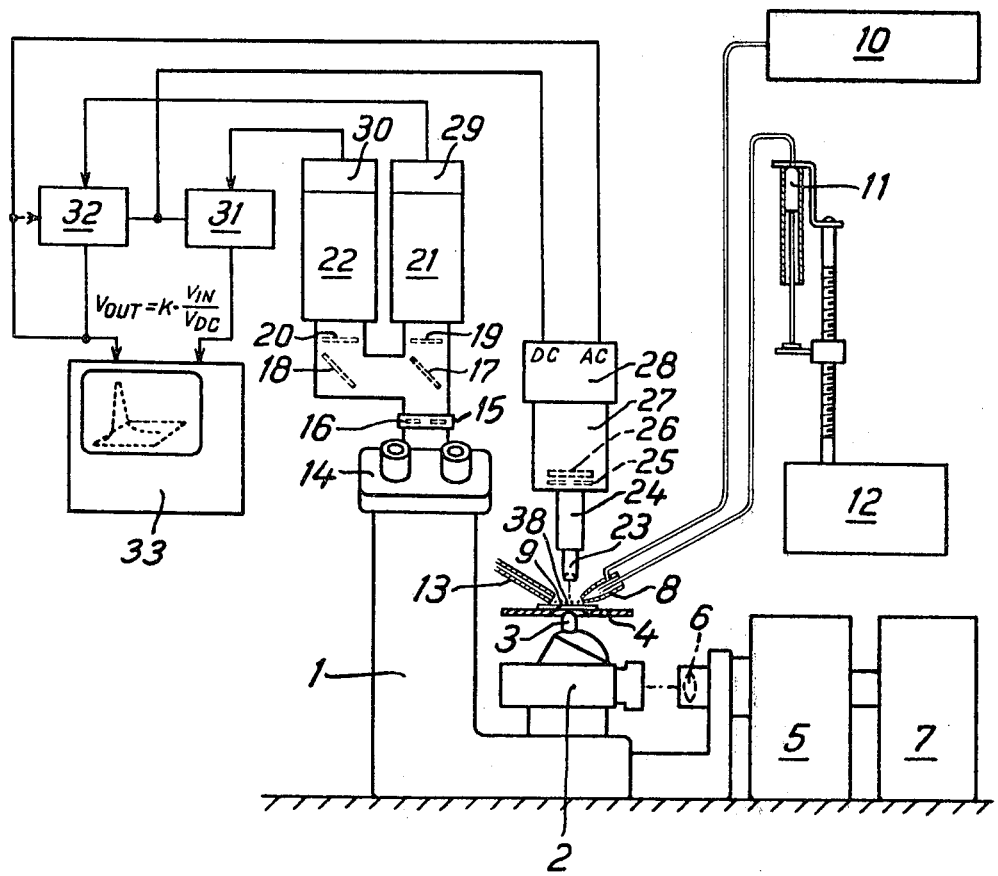
FIG. 1 shows a schematic setup of a complete liquid flow photometer according to the invention and FIG. 2 shows in form of a block diagram the essential features for measurements according to the invention.

FIG. 1 shows an inverted microscope 1 with its Epi-illuminator 2 and first objective 3 below the stage 4. The illuminator receives its light from a Hg- or Xe-lamp 5 via a collector-lens 6. The lamp 5 is fed by a stabilized DC-power-supply 7. On the stage 4 is mounted the liquid flow system as described in the Norwegian patent application No. 791229. The main part of this system is a nozzle 8 positioned under an oblique angle slightly above a cover glass 9. The nozzle 8 is connected to a pressurized sheath fluid 10 and a disposable sample syringe 11 which is pressurized by a variable speed motor 12. The liquid jet leaving the nozzle 8 is converted to a flat, laminar flow moving along the surface of the cover glass 9. Because particles within the sample are centered by hydrodynamic focussing in the liquid jet, they will flow across the cover glass 9 one by one within a narrow sector. The liquid flow will be sucked off from the cover glass 9 by a drainage 13.

Visual observation of the particles and the particles fluorescence light is possible through a binocular 14.

For photometric measurement of the fluorescence light the microscope 1 is followed by a tube 15 which contains a measuring slit 16, a dichromatic mirror 17, a mirror 18 and filters 19, 20. The filters, which transmit different parts of the spectrum, e.g. red and green, for the purpose of spectral measurement, are followed by photomultipliers 21, 22.

Above the stage 4 there is positioned a second objective 23 which has a long focal distance. This objective is connected to a tube 24 which contains also a measuring slit 25, a filter 26 and a light detector 27. The electrical signal of this detector is amplified and devided in a DC and an AC part in an amplifier 28.

The photomultipliers 21, 22 are followed by amplifiers 29,30 and pulse height compensators 31, 32, which are also connected to the DC outlet of the amplifier 28. The output signals of the pulse height compensators 31, 32 are inversely proportional the DC signal of the amplifier 28

$$\left(V_{OUT} = k \frac{V_{IN}}{V_{DC}}\right).$$

The pulse height compensator 32 can alternatively also be connected to the AC outlet of the amplifier 28 so that this AC signal is corrected by the DC signal in the same way as the AC signals from the amplifiers 29,30.

The uncompensated scattered light AC signal and the compensated AC signals (fluorescence and/or scattered light) are then fed to a separate unit for further pulse height analysis, computation, registration etc. FIG. 1 shows for example a dual parameter Multi-Channel-Pulse-Height Analyzer 33 indicating on a screen the number of particles (Z direction) having coinciding scattered and/or fluorescence light intensity (X-Y direction).

Figure 2:
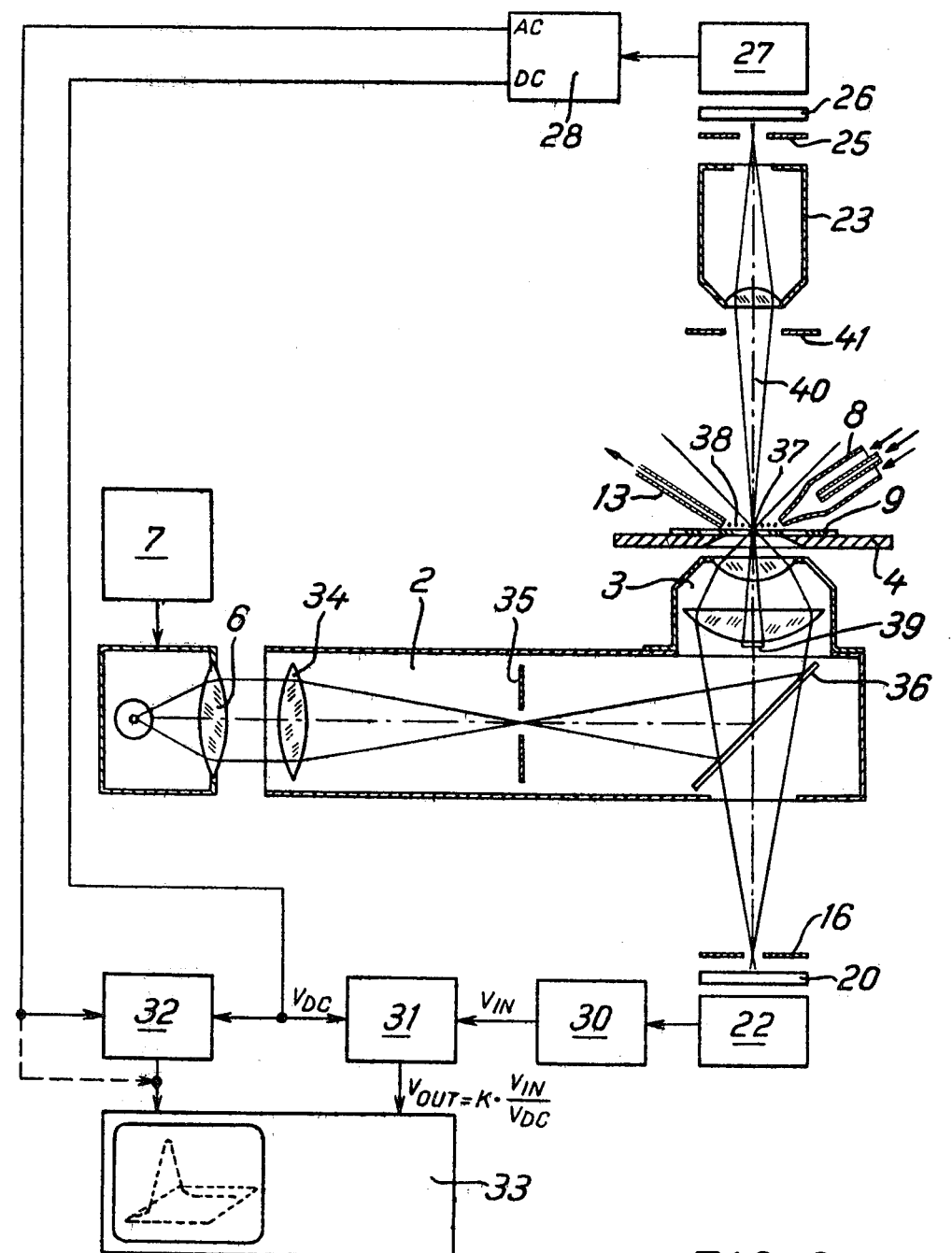

FIG. 2 shows some more details of the essential features. The Epi-illuminator 2 contains a further lens 34, a field diaphragm 35 and a dichromatic mirror 36. This mirror reflects the excitation light via the first objective 3 into the measuring area 37 where the particles 38 flow.

According to the invention the first objective 3 is modified by a central stop 39 in the rear focal plane of the objective 3, This central stop 39 obscures a conically formed sector 40 within the illumination area behind (over) the measuring area 37 of the microscope. Since the objective 3 focusses the excitation light source 5 in the measuring area 37 this results, in connection with the central stop 39, in a dark field critical illumination. If the central stop 39 is perfectly opaque the conically formed sector 40 does not contain excitation light, but only fluorescence and scattered light from the particles 38 passing through the measuring area 37. The second objective 23 is placed behind (above) the measuring area 37 in such a way that its entire aperture falls within the conic, dark sector 40 and thus only catches fluorescence and scattered light. The aperture of the objective 23 can be made to correspond to the sector 40 by an adjustable diaphragm 41 located in front of the objective 23. The measuring slit 25 located in the image plane of the objective 23 limits the light detected by the detector 27 to that part of the measuring area where the fluorescence is measured.

The fluorescence light is eliminated by using a suitable light filter 26 in the light path of the second objective 23. Thus the light falling on the light detector 27 placed behind this filter, will only be scattered light from the particles 38.

According to the present invention the above mentioned central stop 39 is not fully opaque but slightly transparent, that means it has a very faint light transmission.

In this way the above mentioned dark, conic sector 40 will contain a very faint component of direct excitation light also falling on the light detector 27.

The light scattered by the particles 38 appears as short pulses, while the direct excitation light only varies slowly with time. Thus the signal from the light detector 27 behind the second objective 23 will contain two components:

(a) an AC component in the form of short pulses representing the scattered light intensity and
(b) a DC component representing the intensity of the direct excitation light.

Both signals are separated and amplified in the amplifier 28.

The fluorescence light emanating from the particles 38 in the measuring area 37 is collected by the first objective 3 and passes the dichromatic mirror 36. The measuring slit 16 limits the field of the measuring area 37 and the light filters 19 and 20 serve for spectral measurements of the fluorescence light. Because of the dichromatic mirror 36 the signal from the light detector 22 following the first objective 3 will contain only an AC component in form of short pulses representing the fluorescence light intensity. These pulses are amplified in the amplifier 30.

The signal from the light detector 27 and the amplifier 28 representing the above mentioned DC component is fed as a correction signal to the pulse height compensators for the fluorescence light intensity 31 and the scattered light intensity 32. These corrections are made so that the amplification level is inversely proportional to the DC signal $$\left(V_{OUT} = k \frac{V_{IN}}{V_{DC}}\right).$$

As the pulses entering the pulse height compensators are proportional to the intensity of excitation light and thus to the above mentioned DC component, the pulses coming out of the compensators will be independent of this light intensity which is one object of the present invention.

What is claimed is:

1. A liquid flow photometer for fluorescence light and/or scattered light measurement, having a measuring area (37) where particles (38) flow through comprising:
   (a) a fist objective (3) positioned for focussing excitation light (5) in the measuring area (37) and also for collecting fluorescence light emanating from said measuring area, said objective being modified by a slightly transparent central stop (39) placed in the rear focal plane of said objective for causing only a very faint light transmission in a sector of said excitation light,
   (b) a second objective (23) positioned for collecting the light falling within said sector (40) caused by said central stop (39),
   (c) a filter (26) in the light path of said second objective (23) absorbing the fluorescence light emanating from said measuring area (37),
   (d) an adjustable aperture (25) located in the image plane of said second objective (23) limiting the image field of said second objective (23) to the actual width of said measuring area (37),
   (e) light detectors comprising a first light detector positioned for measuring the light intensity collected by said first objective and a second light detector positioned for measuring the light intensity collected by said second objective, and
   (f) electronic amplifiers following said light detectors.

2. A liquid flow photometer as defined in claim 1 wherein said second objective (23) is placed so that its object plane falls in said measuring area (37) and that its aperture falls within said sector of the illumination field (40) caused by said central stop (39).

3. A liquid flow photometer as defined in claim 1 wherein the measurement of scattered light intensity produced by said particles (38) and excitation light intensity in the measuring area (37) is carried out by a common optical system comprising said second objective (23), said filter (26), said adjustable aperture (25), one of said light detectors (27) and one of said electronic amplifiers (28).

4. A liquid flow photometer as defined in claim 3 wherein said electronic amplifier (28) following said light detector (27) in connection with said second objective (23) has separate outlets for the pulsed (AC) part and the constant or slowly varying (DC) part of the signal from said light detector (27), said AC-signal corresponding to the scattered light intensity and said DC-signal corresponding to the excitation light intensity.

5. A liquid flow photometer as defined in claim 4 comprising at least one pulse height compensator (31, 32) correcting the AC-signals, corresponding to the fluorescence light intensity and/or to the scattered light intensity by the DC-signal corresponding to the excitation light intensity in such a way that the electronic amplification is inversely proportional to said DC-signal.

6. A liquid flow photometer as defined in claim 1 further including an adjustable diaphragm positioned to match the size of the aperture of said second objective to said sector caused by said slightly transparent central stop.

* * * * *